United States Patent

Gehlhaus et al.

[11] 4,028,412
[45] June 7, 1977

[54] NOVEL CHELATE FORMERS

[75] Inventors: Jurgen Gehlhaus; Dietrich Erdmann, both of Darmstadt, Germany

[73] Assignee: Merck Patent Gesellschaft mit beschrankter Haftung, Darmstadt, Germany

[22] Filed: Feb. 17, 1976

[21] Appl. No.: 658,507

[30] Foreign Application Priority Data

Feb. 18, 1975 Germany .......................... 2506727

[52] U.S. Cl. .................. 260/566 A; 260/429 C; 260/438.1; 423/24; 252/182
[51] Int. Cl.² ...................................... C07C 131/00
[58] Field of Search ................ 252/182; 260/566 A

[56] References Cited
OTHER PUBLICATIONS

J. Am Chem. Soc. 56, 1148 (1934).
Rec. Trav. Chim. 59, 1141 (1940).
Ber. Dt. Chem. Ges. 70, 23 (1937).

Primary Examiner—Gerald A. Schwartz
Attorney, Agent, or Firm—Millen & White

[57] ABSTRACT

Benzoin oximes of the formula

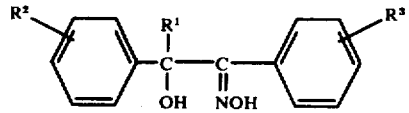

wherein $R^1$ is alkyl of 3 to 16 carbon atoms, alkenyl of 3 or 4 carbon atoms, 3,7-dimethyl-2,6-octadienyl-1, or $-A-S-R^4$; $R^2$ and $R^3$ independently are H, methyl or chlorine; $R^4$ is alkyl or 1 to 8 carbon atoms; and A is alkylene of 3 or 4 carbon atoms, are chelating agents for copper.

8 Claims, No Drawings

NOVEL CHELATE FORMERS

BACKGROUND OF THE INVENTION

This invention relates to a process for selective extraction of copper ions from aqueous solutions with novel benzoin oxime chelate formers into a liquid hydrocarbon.

In recent years, hydrometallurgical processes have achieved increasing importance for recovery of metals, especially for environmental considerations and a relatively low labor requirement. In these processes, the ores are first dissolved in acids or bases. The ore lye obtained is intensively mixed with complex formers dissolved in organic solvents. Depending on the extraction agent and the pH value, only certain metal ions are complexed and transferred to the organic phase. In the specification and claims "extraction agent" means a mixture of the chelate former and a suitable solvent. In this way, the desired metal ions can be separated from impurities. Metal chelates dissolved in the organic phase are subsequently decomposed so that the extraction agent can be recycled for subsequent extractions.

Solvent extraction is widely employed in copper recovery since copper ions form very stable chelates with many extraction agents and the metal value is high. Copper can be separated from other metal ions present in the ore lye, e.g., iron, zinc, cobalt and nickel, as well as other metals, by solvent extraction. Organic phase containing copper chelate is then separated from the ore lye and intensively mixed with dilute mineral acid. With decomposition of the chelate, copper ions are returned to the aqueous phase, whereas the extraction agent is regenerated.

Chelate formers employed for the above process must satisfy various requirements:

a. The chelate former and copper chelate must be very soluble in organic solvents but practically insoluble in water. High solubility in water would increase costs because of losses of chelate formers and/or copper.

b. The chelate former, in certain pH ranges, must complex copper ions selectively. The pH of copper ore lyes is generally below 2.

c. High chemical stability, especially against acids, is required of chelate formers for copper, because most copper ore lyes have pH below 2.

d. The copper chelate should not decompose under the extraction conditions but must be decomposable into its components by treatment with dilute mineral acids or strippers. This requirement is especially important since the copper is usually deposited electrolytically from the acidic strip solution obtained. If acid concentration of the strip solution is too high, the electrodes dissolve partially and contaminate the electrolytic copper with lead.

e. It is very important that the emulsions formed by mixing extraction agent with the ore lye separate quickly so as to avoid long settling times.

f. Rapid chelate formation is critical for economic operation of a continuous countercurrent extraction plant.

Known chelate formers for copper ion extraction only fulfill the above requirements partially. For example, derivatives of 8-hydroxy-quinoline and their copper chelates are only moderately soluble in conventional solvents for solvent extraction. They require relatively strong mineral acids for stripping. Because of their relatively basic properties, they extract acid during stripping so that the extraction agent becomes contaminated with acid.

Aliphatic hydroxyoximes have also been used as chelate formers in extraction agents. Aliphatic hydroxyoximes do not operate quantitatively below pH 1.3. Substituted o-hydroxybenzophenone oximes, which are very effective below pH 1.3, have the disadvantage that chelate formation requires a long time and the copper complex formed can be decomposed only with relatively strong mineral acids.

These disadvantages do not occur with new chelate formers of this invention. For solvent extraction of copper ions according to the present invention, a compound of Formula I, or mixture thereof, can be used.

SUMMARY OF THE INVENTION

In a compositional aspect, this invention relates to novel benzoin oximes of Formula I

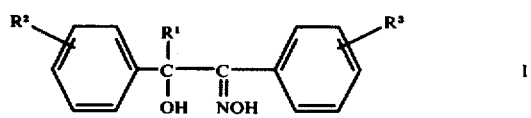

wherein $R^1$ is alkyl of 3 to 16 carbon atoms, alkenyl of 3 or 4 carbon atoms, 3,7-dimethyl-2,6-octadienyl-1, or $-A-S-R^4$; $R^2$ and $R^3$ independently are H, methyl or chlorine; $R^4$ is alkyl of 1 to 8 carbon atoms and A is alkylene of 3 or 4 carbon atoms.

In a process aspect, this invention relates to a process for extracting copper ions from aqueous solutions by the steps of:

a. forming a chelate of copper ion with a benzoin oxime in an extraction reagent comprising a hydrocarbon solvent and a benzoin oxime of Formula VI

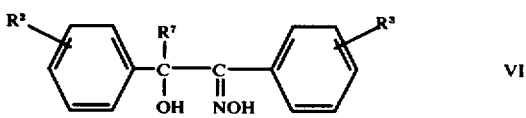

wherein $R^7$ is methyl, ethyl or $R^1$ and $R^1$, $R^2$ and $R^3$ are as in Formula I;

b. extracting the chelate from the aqueous solution with the hydrocarbon solvent; and c. treating said chelate extracted into said hydrocarbon solvent with an aqueous acid, whereby copper ions are transferred to an aqueous phase.

In another compositional aspect, this invention relates to a reagent for the extraction of copper ions from aqueous solutions, comprising a liquid hydrocarbon and a benzoin oxime of Formula VI, as above.

In another aspect, this invention relates to a process for preparing benzoin oximes of Formula I wherein a. a compound of Formula II

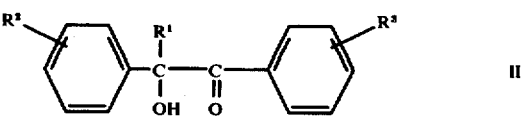

wherein $R^1$, $R^2$ and $R^3$ are as above is treated with hydroxylamine or a hydroxylamine salt;

b. a compound of Formula III

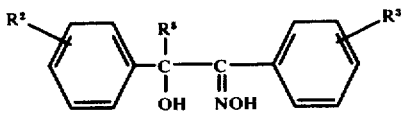

III wherein $R^5$ is unsaturated alkyl of 3 to 16 carbon atoms and $R^2$ and $R^3$ are as above is hydrogenated; or c. a compound of Formula IV

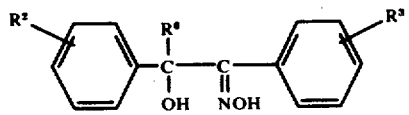

IV wherein $R^6$ is an alkenyl of 3 or 4 carbon atoms and $R^2$ and $R^3$ are as above is reacted with a compound of Formula V

 R'SH    V wherein $R^4$ is as above.

DETAILED DESCRIPTION

In the Formulae, $R^1$ is alkyl of 3 to 16 carbon atoms, preferably unbranched. Examples of preferred alkyl are propyl, butyl, pentyl, hexyl, octyl, decyl, dodecyl, tetradecyl and hexadecyl. If alkyl radicals are branched, methyl branches are preferred. Preferred branched alkyl include isobutyl, isopentyl, 1,1,3,3-tetramethylbutyl and 2,4,4-trimethylpentyl.

$R^1$ can also be alkenyl of 3 or 4 carbon atoms. Alkenyl include 1-propenyl, 2-methyl-1-propenyl and 2-methyl-2-propenyl radical, as well as allyl and crotyl. Allyl and crotyl are preferred. $R^1$ can also be 3,7-dimethyl-2,6-octadienyl-1.

$R^1$ can also be -A-S-$R^4$, wherein A is alkylene of 3 or 4 carbon atoms, e.g., trimethylene, tetramethylene, 1,2-propandiyl, 2,2-propandiyl, 1,2-butandiyl, 1,3-butandiyl, 2,3-butandiyl or 2-methyl-1,3-propandiyl. Unbranched alkylene, i.e., trimethylene and tetramethylene, are preferred.

$R^4$ is alkyl, preferably unbranched alkyl of 1 to 8 carbon atoms, most preferably methyl, ethyl, butyl, hexyl or octyl. When $R^4$ is a branched alkyl of 1 to 8 carbon atoms, it preferably has methyl branches, e.g., those given above for $R^1$.

Especially preferred are compounds of Formula I in which at least one $R^1$ to $R^4$ or A has one of the preferred structures.

Some of these preferred groups of compounds have the following Formulae, which otherwise correspond to Formula I:

a. $R^1$ is alkyl of 3-16 carbon atoms;
b. $R^1$ is propyl, butyl, hexyl, octyl, decyl, or dodecyl, and $R^2$ and $R^3$ are H;
c. $R^1$ is alkenyl of 3-4 carbon atoms;
d. $R^1$ is -A-S-$R^4$;
e. $R^1$ is -A-S-$R^4$; A is trimethylene; $R^4$ is methyl, ethyl, butyl, hexyl or octyl, and $R^2$ and $R^3$ are H;
f. $R^2$ and $R^3$ each are H or p-CH$_3$; and
g. $R^2$ and $R^3$ are H.

Known compounds 2-hydroxy-1,2-diphenylpropanone oxime-1 and 2-hydroxy-1,2-diphenylbutanone oxime-1 can be used for solvent extraction by this invention. The two phenyl radicals can be substituted by $R^2$ and/or $R^3$.

These compounds can be included with compounds of Formula I in Formula VI. Known compounds of Formula VI can be used alone, with other known compounds of Formula VI or with new compounds of Formula I for solvent extraction according to the invention.

New benzoin oximes of Formula I can be used for the selective extraction of copper ions from aqueous solutions. Compounds of Formula VI also permit selective extraction of copper ions from aqueous solutions which are strongly acidic, e.g., ore leaches. Compounds of Formulae VI and I are not chemically changed at low pH values, even over comparatively long periods of time, but the copper complexes obtained can be split quantitatively with relatively dilute mineral acid.

Therefore, the benzoin oximes of Formulae I or VI can be employed as chelate formers for selective extraction of copper from ore leaches on a large scale.

The process for extraction of copper ions from aqueous solutions with chelate formers in the presence of a liquid hydrocarbon, separating the copper-containing organic phase and transferring copper ions into an aqueous phase by treatment with an aqueous acid, employs an extraction step with a benzoin oxime of Formula VI, preferably of Formula I, as chelate former.

Thus, the invention is also a process for extraction of copper ions from aqueous solutions which chelate formers in the presence of a liquid hydrocarbon, separation of the copper-containing organic phase and transfer of the copper ions into an aqueous phase by treatment with an aqueous acid, wherein extraction with benzoin oximes of Formula VI is done at a pH value below 1.3.

Use of benzoin oximes of the Formulae VI or I as chelate formers in solvent extraction of aqueous copper salt solutions is also the subject of the invention.

An agent for extraction of copper ions from aqueous solutions consists of a liquid hydrocarbon solvent and a chelate former of Formula VI or of Formula I.

The following chelate formers are especially preferred for carrying out copper ion extraction:

2-hydroxy-1,2-diphenylpentanone oxime-1;
2-hydroxy-1,2-diphenylhexanone oxime-1;
2-hydroxy-1,2-diphenyloctanone oxime-1;
2-hydroxy-1,2-diphenyldecanone oxime-1;
2-hydroxy-1,2-diphenyldodecanone oxime-1;
2-hydroxy-1,2-diphenyltetradecanone oxime-1;
2-hydroxy-1,2-diphenyl-5,9-dimethyldecadiene-(4,8)-one oxime-1;
2-hydroxy-1,2-diphenyl-5-thiobutylpentanone oxime-1;
2-hydroxy-1,2-diphenyl-5-thiooctylpentanone oxime-1;
2-hydroxy-1,2-di-p-tolylpentanone oxime-1;
2-hydroxy-1,2-di-p-tolyl-5-thiobutylpentanone oxime-1;
2-hydroxy-1,2-di-p-tolyl-5-thiooctylpentanone oxime-1, and
2-hydroxy-1,2-di-(p-chlorophenyl)-pentanone oxime-1.

For copper ion extraction, compounds of Formula VI or Formula I, especially preferred compounds of Formula I, are dissolved in solvents. Solvents for this process include inert hydrocarbons, e.g., liquid aliphatic, cycloaliphatic, aromatic or araliphatic hydrocarbons, and chlorinated derivatives thereof. Certain mineral oil fractions are preferred, e.g., light Diesel oil or kerosene, which boil in the ranges 110° and 250°, respectively. If possible, solvents with high flash points should be selected. Chlorinated solvents include polychlorinated aliphatic hydrocarbons, e.g., 1,2-dichloroethane, trichloroethylene, perchlorobutadiene, and chlorinated aromatic hydrocarbons, e.g., chlorobenzene or 1-chloronaphthalene.

The concentration of chelate former in the extraction agent is above 2%, preferably, between 20 and 10% by weight. At higher concentrations, solubilizing agents, for example, alkylphenols, e.g., nonylphenol, or long chain aliphatic alcohols, e.g., isooctanol or isodecanol can be used. Better solubility of chelate former and complex in the organic phase is thereby achieved. The addition of such compounds often also results in more rapid phase separation during extraction.

A decisive advantage of solvent extraction with compounds of Formula VI is the fact that the copper ions can be extracted from strongly acidic ore lyes with low pH values. Thus, the chelate formers also operate satisfactorily at pH 0.7 for comparatively long periods without changing chemically.

Quantitative cleavage of the copper chelates obtained can be achieved with relatively dilute mineral acids. Mineral acids include hydrohalic acids, preferably HCl or HBr; oxygen acids, preferably sulfuric acid; nitric acid and phosphoric acid. Concentrations of dilute aqueous mineral acids are between 2 and 20 wt.%, preferably between 5 and 10 wt.%. Thus copper ions can be extracted back into the aqueous phase from the organic phase of the extraction agent quantitatively with 5 to 10 wt.% sulfuric acid. The low concentration of mineral acid reduces the danger of dissolving the electrode in subsequent electrolytic copper deposition and prevents hydrolytic decomposition of the chelate former.

Chelate formers of Formula VI useable according to the invention are extremely selective. Selective extraction of copper ions from ore lyes containing up to twice as much zinc, iron, cobalt, nickel or other metal ions as copper is successful. This is very important because transfer of even small amounts of coextractable foreign ions in the back extraction to the copper salt solution for electrolysis would decisively reduce the economy of electrolytic deposition.

Compounds of Formula I and the corresponding starting compounds are prepared by known reaction conditions, as given in the literature, e.g., HOUBEN-WEYL, "Methoden der organischen Chemie," Georg-Thieme-Verlag, Stuttgart.

Reaction of a compound of Formula II with hydroxylamine or a salt of hydroxylamine is done in a solvent, preferably a polar solvent, for example, a lower aliphatic alcohol, such as methanol, ethanol or isopropyl alcohol; water or mixtures of water and the above solvents. Suitable salts of hydroxylamine include acid-addition salts with mineral acids, preferably, the hydrochloride and the sulfate.

The reaction is preferably carried out in the presence of an acidic or basic catalyst. Suitable catalysts include protonic acids, for example, mineral acids, such as sulfuric acid or HCl; organic acids, e.g., lower aliphatic carboxylic acids, such as formic acid or acetic acid; and sulfonic acids, such as p-toluenesulfonic acid. Mineral acids are preferred.

Basic catalysts, include alkali metal hydroxides, e.g., NaOH or KOH; amines, e.g., trimethylamine or pyridine; and basic salts, e.g., potassium carbonate or sodium acetate.

Reactions temperatures are between about room temperature and the boiling point of the reaction mixture, preferably between about 40° and 80° C. Reaction times are not critical and depend on reaction temperature; they are between approximately 2 and 8 hours.

Compounds of Formula II are obtained from the corresponding benzoins, which contain a hydrogen atom instead of $R^1$, by reaction with a compound of Formula VII $$R^1 - X \qquad \text{VII}$$

wherein X is Cl, Br, I or arylsulfonyloxy and $R^1$ is as above.

In compounds of Formula VII, arylsulfonyloxy means an isocyclic arylsulfonyloxy radical of 6 to 10 carbon atoms, preferably p-tolylsulfonyloxy as well as the p-bromophenylsulfonyloxy and $\alpha$- and $\beta$-naphthylsulfonyloxy.

Reactions of benzoins, which otherwise correspond to Formula II, but which contain a hydrogen atom instead of $R^1$, with a compound of Formula VII preferably takes place in an inert organic solvent. Aprotic dipolar solvents are especially preferred, for example, dimethyl sulfoxide, dimethyl formamide, acetonitrile, tetrahydrothiophene-S,S-dioxide, tetramethylurea or hexamethylphosphoric acid triamide. The reaction is carried out in the presence of basic catalysts. Preferably 10 to 30 wt.% of aqueous alkali metal hydroxide solutions, especially of NaOH, are used. Reaction temperatures are between about 10° and about 40°, preferably room temperature.

In an especially preferred variant, compounds of Formula II are obtained by reaction of a benzoin which otherwise corresponds to the Formula I, but which contains a hydrogen atom instead of $R^1$, with allyl chloride or bromide in an aprotic dipolar solvent in the presence of a basic catalyst and subsequent reaction of the 2-hydroxy-1,2-diaryl-4-pentenone-1 obtained with a compound of Formula V. One can hydrogenate 2-hydroxy-1,2-diaryl-4-pentenone-1 catalytically and get a compound of Formula II ($R^1$ is propyl).

If crotyl chloride or crotyl bromide is used as alkenylation agent instead of an allyl compound, one obtains, in a corresponding reaction sequence, compounds of Formula II in which $R^1$ is butyl or following reaction with $R^4SH$, $-A-S-R^4$, wherein A is 1,2-butandiyl or 1,3-butandiyl.

Compounds of Formula III are obtained by reaction of a benzoin oxime which otherwise corresponds to Formula I, but in which a hydrogen atom is present instead of $R^1$, with a compound of Formula VIII $$R^5 - X \qquad \text{VIII}$$

wherein $R^5$ and X are as above.

Reaction conditions for the alkenylation correspond to those stated above for preparation of a compound of Formula II.

Compounds of Formula I are obtained from the compounds of Formula III by reaction with a hydrogenating agent. Catalytically activated hydrogen is preferred as hydrogenating agent. Suitable catalysts are activated metals, possibly on a carrier. Examples are Raney nickel, Raney cobalt, platinum or palladium. Platinum oxide, possibly on calcium sulfate, can also be used as catalyst for the hydrogenation. The hydrogenation is carried out in an inert organic solvent. Suitable solvents are lower aliphatic alcohols, e.g., methanol or ethanol; lower alkanecarboxylic acids, e.g., acetic acid; lower aliphatic carboxylic acid esters, preferably ethyl acetate; or ethers, e.g., diethyl ether, tetrahydrofuran or dioxane. Reaction temperatures are between room temperature and 80° C. Usually, one operates at 1 atm. up to about 5 atm. The hydrogenation of a compound of Formula III is stopped as soon as the calculated amount of hydrogen has been taken up.

Compounds of Formula IV are obtained from compounds which otherwise correspond to Formula II, but which, contain the $R^6$ instead of $R^1$, by reaction with hydroxylamine or a salt of hydroxylamine. Suitable reaction conditions for oxime formation have been described above. Compounds of the Formula V are known or can be prepared analogously to known methods, e.g., from compounds of Formula $R^4$-X by reaction with sodium hydrogen sulfide.

Addition of a compound of Formula V to a compound of Formula IV preferably takes place under radical conditions. Generally, reaction components are irradiated at temperatures between 60° and 130° with a high pressure mercury lamp. Reaction times are between about 4 and about 12 hours. The reaction can be done in an inert organic solvent, preferably a hydrocarbon, for example, toluene or xylene. However, one can also initiate and carry out the radical addition with a radical former, for example, an aliphatic azo compound, such as azobisisobutyronitrile.

The preparation of compounds of Formula I according to the invention are described in the following by way of example.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. One boils 388 g. of 2-hydroxy-1,2-diphenylpentanone-1, 425 g. of hydroxylamine hydrochloride, 485 g. of pyridine and 1.2 l. of ethanol for 5 hours. The cooled mixture is diluted with 1.2 l. of water and extracted with toluene. The toluene phase is washed with dilute hydrochloric acid; the solvent is distilled off; and the residue is dissolved with warming in 1.5 l. of petroleum ether and 100 ml. of toluene. After cooling, 2-hydroxy-1,2-diphenylpentanone oxime-1 is filtered off, m.p. 94°–95°.

b. The starting product is obtained as follows: one drops into a stirred solution of 428 g. of benzoin in 4 l. of dimethyl sulfoxide, under nitrogen, within 35 minutes, 153 g. of allyl chloride and 400 ml. of 20% aqueous NaOH, while the temperature is maintained between 20° and 25°. One stirs for 3 hours more, pours the reaction mixture into a mixture of 500 ml. of concentrated aqueous hydrochloric acid and 500 ml. of water, extracts with diethyl ether, dilutes the aqueous phase with 2 l. of water, and extracts with toluene. The combined organic phases are dried over sodium sulfate. After distilling off solvent and recrystallization of the residue from petroleum ether/diethyl ether (1:1), α-allylbenzoin, m.p. 92°–93°, is obtained.

c. One hydrogenates 500 g. of α-allylbenzoin dissolved in 5 l. of tetrahydrofuran, in the presence of 80 g. of Raney nickel at room temperature until hydrogen uptake ceases. One filters off catalyst and removes solvent to obtain, after recrystallization of the residue from 80% aqueous methanol, 2-hydroxy-1,2-diphenylpentanone-1, m.p. 71°–73°.

EXAMPLE 2 a. One adds dropwise to 637 g. of benzoin, dissolved in 6 l. of dimethyl sulfoxide, at 20°–25°, with stirring and under nitrogen, 748 g. of 1-bromodecane and 600 ml. of 20% aqueous sodium hydroxide solution. The mixture is stirred for 12 hours more. The oil formed is separated and the DMSO phase extracted with petroleum ether. The petroleum ether solution and the oil are combined and dried over magnesium sulfate. Solvent is removed and, after recrystallization of the residue from petroleum ether, 2-hydroxy-1,2-diphenyltetradecanone-1, m.p. 80°–82°, is obtained.

b. One boils 247 g. of 2-hydroxy-1,2-diphenyltetradecanone-1 and 181 g. of hydroxylamine hydrochloride for 4 hours in a mixture of 205 g. of pyridine and 650 ml. of ethanol. The cooled reaction mixture is mixed with water and extracted with diethyl ether. One dries the organic phase over sodium sulfate, distills off solvent and obtains, after recrystallizing the residue from petroleum ether, 2-hydroxy-1,2-diphenyl-tetradecanone oxime-1, m.p. 80°–81°.

Reaction of benzoin with the corresponding compounds of Formula VII and subsequent treatment of the hydroxyketone obtained with hydroxylamine hydrochloride yields the following compounds of Formula I:

2-hydroxy-1,2-diphenyl-hexanone oxime-1, m.p. 86°–87°;
2-hydroxy-1,2-diphenyl-octanone oxime-1, m.p. 96°–98°;
2-hydroxy-1,2-diphenyl-decanone oxime-1, m.p. 81°–83°;
2-hydroxy-1,2-diphenyl-dodecanone oxime-1, m.p. 76°–78°; and
2-hydroxy-1,2-diphenyl-5,9-dimethyldecadien-(4,8)-one oxime, m.p. 66°.

EXAMPLE 3

One irradiates a mixture of 550 g. of α-allylbenzoin and 440 ml. of butanethiol-1 for 8 hours with a mercury high pressure burner Q 81 (Quarzlampen GmbH, Hanau), whereupon the temperature of the reaction mixture increases to 100°. Excess butanethiol is distilled off and the residue boiled for 5 hours, with stirring, with 619 g. of hydroxylamine hydrochloride, 704 g. of pyridine and 2 l. of ethanol. After cooling, the reaction mixture is diluted with 2 l. of water and extracted with diethyl ether. The combined ether extracts are washed with dilute aqueous hydrochloric acid and dried over sodium sulfate. After distilling off of the solvent and recrystallization of the residue from petroleum ether-toluene (1:1), one obtains 2-hydroxy-1,2-diphenyl-5-thiobutylpentanone oxime-1, m.p. 77°–79°.

2-Hydroxy-1,2-diphenyl-5-thiooctylpentanone-1 obtained from α-allylbenzoin and octanethiol-1 is reacted with hydroxylamine hydrochloride to give 2-hydroxy-1,2-diphenyl-5-thiooctylpentanone oxime-1, m.p. 48°–50°.

EXAMPLE 4

By the procedure of Example 1, p,p'-dimethylbenzoin is treated with allyl chloride in the presence of aqueous sodium hydroxide solution to give 2-hydroxy-1,2-di-p-tolyl-4-penten-1-one, m.p. 38°–40°. This product is hydrogenated in the presence of Raney nickel to 2-hydroxy-1,2-di-p-tolylpentane-1-one which, by reaction with hydroxylamine hydrochloride, gives 2-hydroxy-1,2-di-p-tolylpentanone oxime-1, m.p. 113°–114°.

EXAMPLE 5

2-Hydroxy-1,2-di-p-tolyl-4-penten-1-one, by reaction with butanethiol and subsequent reaction of the product with hydroxylamine hydrochloride by the method of Example 3 is converted to 2-hydroxy-1,2-di-p-tolyl-5-thiobutylpentanone oxime-1, m.p. 74°–76°.

EXAMPLE 6

In the manner of Example 1, p,p'-dichlorobenzoin and allyl chloride, in the presence of sodium hydroxide, produce a benzoin, hydrogenation of which in the presence of Raney nickel and reaction of the product obtained with hydroxylamine hydrochloride, gives 2-hydroxy-1,2-di-p-chlorophenylpentanone oxime-1, m.p. 108°–109°.

EXAMPLE 7

By the method of Example 1, one obtains from α-allylbenzoin and hydroxylamine hydrochloride, in the presence of pyridine, 2-hydroxy-1,2-diphenyl-4-penten-1-one oxime.

EXAMPLE 8

200 g. of 2-hydroxy-1,2-diphenyl-4-pentenone oxime-1 and 300 ml. of butanethiol-1 is irradiated for 6 hours with a mercury high pressure lamp Q 81 (Quarzlampen GmbH, Hanau), whereupon the temperature of the reaction mixture increases to 100°. Excess butanthiol is distilled off and the residue recrystallized from petroleum ether-toluene (1:1). 2-Hydroxy-1,2-diphenyl-5-thiobutylpentanone oxime-1, m.p. 77°–79°, is obtained.

In Examples 9 to 11, the use of chelate formers of Formula VI for solvent extraction of copper ions is illustrated.

EXAMPLE 9

12 mMol of 2-hydroxy-1,2-di-p-tolylpropanone oxime-1 were dissolved in 100 ml. of a mixture of Diesel oil and nonylphenol (7:3) and were stirred portionwise with 10 ml. of a copper lye (pH 0.85) for 10 minutes. The copper lye contained, per liter: 25 g. of copper, 50 g. of zinc, 1 g. of iron, 0.6 g. of cobalt, 150 g. of sodium, and sulfate and chloride. The extraction was carried out by stirring 10 ml. of copper lye for 10 minutes with successive portions of one third of the above extraction solution. The copper content of the aqueous phase, which was pink due to cobalt, was determined by atom absorption spectroscopy.

The organic copper extracts were combined and stirred for 10 minutes with four successive portions of 25 ml. of 10% sulfuric acid. Copper content of the aqueous phase was determined as above.

1st cycle

After three extraction steps, 4 mg. of Cu remained in the copper lye: that is, of 250 mg. of Cu, 246 mg. had been extracted. Yield: 98%.

Strip: After 4 stripping steps, 226 mg. of Cu had been extracted back into the aqueous phase. Yield: 92%.

The organic phase, freed of copper in this way, was subjected to the extraction-strip cycle three more times to test its long-term behavior.

2nd cycle

After 3 extractions steps, 6 mg. of Cu remained in the copper lye; of 250 mg. of Cu, 244 mg. had been extracted. Yield: 98%.

Strip: After 4 stripping steps, 221 mg. of Cu were extracted back into the aqueous phase. Yield: 90%.

3rd cycle

After 3 extraction steps, 8 mg. of Cu remained in the copper lye. Thus, of 250 mg. of Cu, 242 mg. had been extracted. Yield: 97%.

Strip: After 4 stripping steps, 215 mg. of Cu were extracted back into the aqueous phase. Yield: 89%.

4th cycle

After 3 extraction steps, 9 mg. of Cu remained in the copper lye. Of 250 mg. of Cu, 241 mg. had been extracted. Yield: 97%.

Strip: After 4 stripping steps, 219 mg. of Cu were extracted back into the aqueous phase. Yield: 91%.

EXAMPLE 10

An extraction solution was prepared from 12 mMol of 2-hydroxy-1,2-diphenylpentanone oxime-1 and 100 ml. of a mixture of nonylphenol and Diesel oil (3:7). The copper lye of Example 1 (pH 0.85) was extracted as described above. Stripping was done three 25-ml. portions of 6% sulfuric acid and the total amount of copper recovered determined. Four more extraction-strip cycles were carried out with the stripped extraction solution. Results are summarized in the following Table:

| CYCLE | EXTRACTION | STRIP |
|---|---|---|
| I | 136 mg. Cu 54% | 123 mg. Cu 90% |
| II | 128 mg. Cu 51% | 118 mg. Cu 92% |
| III | 133 mg. Cu 53% | 126 mg. Cu 95% |
| IV | 137 mg. Cu 54% | 127 mg. Cu 93% |
| V | 126 mg. Cu 51% | 122 mg. Cu 97% |

Atom absorption spectroscopy indicated that no zinc, cobalt or iron had been co-extracted.

EXAMPLE 11

In a countercurrent mixer-settler extraction plant, copper lye of Example 1 was continuously extracted with a solution of 300 g. of 2-hydroxy-1,2-ditolylthiobutylpentanone oxime-1 in 0.9 liter of nonylphenol and 5.4 liter of propylbenzene in 3 steps. Other alkylbenzenes or mixtures thereof, preferably with propylbenzene, can also be used. The organic phase laden with copper was stripped with 9% sulfuric acid in 3 steps. The circulation rate of organic phase through extraction and stripping regions was to 6.5 liters per hour, of copper lye 0.6 liters per hour and stripping acid 2 liters per hour. The plant ran continuously for 8 days. A 1 ml. sample of the extracted residual aqueous solution was removed daily and the amount of unextracted copper therein determined by atom absorption spectroscopy. Results are in the Table:

| Day | Residual Copper in mg./ml. | Copper Extracted in % |
|---|---|---|
| 1st day | 2.5 mg. | 90% |
| 2nd day | 2.6 mg. | 89% |
| 3rd day | 2.5 mg. | 90% |
| 4th day | 2.5 mg. | 90% |
| 5th day | 2.7 mg. | 89% |
| 6th day | 3.2 mg. | 87% |
| 7th day | 3.0 mg. | 88% |
| 8th day | 2.8 mg. | 89% |

Extracted copper in the organic phase could be transferred quantitatively into the stripping solution.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can made various changes and modifications of the invention to adapt it to various usages and conditions.

What is claimed is:
1. A benzoin of oxime of formula

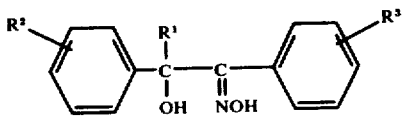

wherein $R^1$ is -A-S-$R^4$; $R^2$ and $R^3$ independently are H, methyl or chlorine; $R^4$ is alkyl of 1 to 8 carbon atoms and A is alkylene of 3 or 4 carbon atoms.

2. A benzoin oxime of claim 1, wherein A is trimethylene; $R^4$ is methyl, ethyl, butyl, hexyl or octyl; and $R^2$ and $R^3$ are H.

3. A benzoin oxime of claim 1, wherein $R^2$ and $R^3$ each are H or p-$CH_3$.

4. A benzoin oxime of claim 1, wherein $R^2$ and $R^3$ are H.

5. A compound of claim 1, 2-hydroxy-1,2-diphenyl-5-thiobutylpentanone-oxime-1.

6. A compound of claim 1, 2-hydroxy-1,2-diphenyl-5-thiooctylpentanone-oxime-1.

7. A compound of claim 1, 2-hydroxy-1,2-di-p-tolyl-5-thiobutylpentanone-oxime-1.

8. A solution of a compound of claim 1 in a liquid hydrocarbon.

* * * * *